United States Patent
Fung et al.

(10) Patent No.: US 10,238,304 B2
(45) Date of Patent: *Mar. 26, 2019

(54) SYSTEM AND METHOD FOR DETERMINING CHANGES IN A BODY STATE

(71) Applicant: Honda Motor Co., Ltd., Tokyo (JP)

(72) Inventors: Kin C. Fung, Dublin, OH (US);
Timothy J. Dick, Dublin, OH (US);
Charles William Hall, Jr., Hilliard, OH (US)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,051

(22) Filed: Jul. 8, 2016

(65) Prior Publication Data

US 2016/0317042 A1    Nov. 3, 2016

Related U.S. Application Data

(63) Continuation of application No. 13/843,077, filed on Mar. 15, 2013, now Pat. No. 9,420,958.

(51) Int. Cl.
*A61B 5/04* (2006.01)
*A61B 5/024* (2006.01)
(Continued)

(52) U.S. Cl.
CPC ............ *A61B 5/024* (2013.01); *A61B 5/0245* (2013.01); *A61B 5/02405* (2013.01);
(Continued)

(58) Field of Classification Search
CPC ..... A61B 5/024; A61B 5/6893; A61B 5/7239; A61B 5/02405; A61B 5/0456; A61B 5/0245; A61B 5/02416; A61B 8/02
(Continued)

(56) References Cited

U.S. PATENT DOCUMENTS 5,609,158 A    3/1997    Chan
5,682,901 A    11/1997    Kamen
(Continued)

FOREIGN PATENT DOCUMENTS

DE    10248894    5/2004
DE    69730298    1/2005
(Continued)

OTHER PUBLICATIONS

Office Action of U.S. Appl. No. 14/851,753 dated Sep. 27, 2016, 95 pages.
(Continued)

*Primary Examiner* — Sanjay Cattungal
(74) *Attorney, Agent, or Firm* — Rankin, Hill & Clark LLP

(57) ABSTRACT

A method and a system for determining changes in a body state of an individual including receiving a signal from a monitoring system, where the signal indicates a measurement of cardiac activity of the individual over a period of time and determining at least one signal feature, where the signal feature is a reoccurring event of the signal over the period of time. The method also includes determining a first interval between two successive signal features and determining a second interval between two successive first intervals. A derivative is calculated based on the second interval. Changes in the body state are identified based on the derivative.

23 Claims, 10 Drawing Sheets

(51) Int. Cl.
  *A61B 5/0245*  (2006.01)
  *A61B 5/0456*  (2006.01)
  *A61B 8/02*  (2006.01)
  *A61B 5/00*  (2006.01)

(52) U.S. Cl.
  CPC ........ *A61B 5/02416* (2013.01); *A61B 5/0456* (2013.01); *A61B 5/6893* (2013.01); *A61B 5/7239* (2013.01); *A61B 8/02* (2013.01)

(58) Field of Classification Search
  USPC ................ 600/407, 437, 473–480, 508–530
  See application file for complete search history.

(56) References Cited

U.S. PATENT DOCUMENTS

| | | |
|---|---|---|
| 6,361,503 B1 | 3/2002 | Starobin et al. |
| 6,663,572 B2 | 12/2003 | Starobin et al. |
| 7,062,313 B2 | 6/2006 | Nissila |
| 7,149,653 B2 | 12/2006 | Bihler et al. |
| 7,225,013 B2 | 5/2007 | Geva et al. |
| 7,953,477 B2 | 5/2011 | Tulppo et al. |
| 8,019,407 B2 | 9/2011 | Lian et al. |
| 9,751,534 B2 | 9/2017 | Fung et al. |
| 2003/0149354 A1 | 8/2003 | Bakharev |
| 2003/0171684 A1 | 9/2003 | Vasin et al. |
| 2004/0088095 A1 | 5/2004 | Eberle et al. |
| 2004/0133082 A1 | 7/2004 | Abraham-Fuchs et al. |
| 2005/0033189 A1 | 2/2005 | McCraty et al. |
| 2005/0155808 A1 | 7/2005 | Braeuchle et al. |
| 2005/0256414 A1 | 11/2005 | Kettunen et al. |
| 2006/0122478 A1 | 6/2006 | Sliepen et al. |
| 2006/0287605 A1 | 12/2006 | Lin et al. |
| 2007/0159344 A1 | 7/2007 | Kisacanin |
| 2008/0027341 A1 | 1/2008 | Sackner et al. |
| 2009/0284361 A1 | 11/2009 | Boddie et al. |
| 2011/0046498 A1 | 2/2011 | Klap et al. |
| 2011/0112442 A1 | 5/2011 | Meger et al. |
| 2011/0137200 A1 | 6/2011 | Yin et al. |
| 2012/0071775 A1 | 3/2012 | Osorio et al. |
| 2012/0116198 A1 | 5/2012 | Veen et al. |
| 2012/0197091 A1 | 8/2012 | Nakano |
| 2012/0290215 A1 | 11/2012 | Adler et al. |
| 2013/0245886 A1 | 9/2013 | Fung et al. |
| 2014/0121927 A1 | 5/2014 | Hanita |
| 2014/0163374 A1 | 6/2014 | Ogasawara et al. |

FOREIGN PATENT DOCUMENTS

| | | |
|---|---|---|
| DE | 102008042342 | 4/2010 |
| DE | 202012001096 | 5/2012 |
| DE | 102013010928 | 12/2014 |
| EP | 2591969 | 5/2013 |
| JP | 11151231 | 6/1999 |
| JP | 2010008268 | 1/2010 |
| JP | 2011022738 | 2/2011 |
| JP | 2012152458 | 8/2012 |

OTHER PUBLICATIONS

Office Action of U.S. Appl. No. 14/851,753 dated Dec. 21, 2016, 12 pages.
Office Action of U.S. Appl. No. 14/851,753 dated Mar. 22, 2017, 14 pages.
German Patent and Trademark Office Search Report of DE Serial No. 10 2014 204 671.8 dated Oct. 21, 2014, 10 pages.
English Translation of German Patent and Trademark Office Search Report of DE Seril No. 10 2014 204 671.8 dated Oct. 21, 2014, 8 pages.
International Search Report and Written Opinion of PCT/US2015/037019 dated Nov. 2, 2015, 12 pages.
Office Action of U.S. Appl. No. 13/843,077 dated Jan. 16, 2015, 15 pages.
Office Action of U.S. Appl. No. 13/843,077 dated Jul. 29, 2015, 8 pages.
Office Action of Japanese Patent Application No. 2014-047880 w/ English machine translation, dated Oct. 29. 2017, 5 pages.
Extended European Search Report of related application No. EP 15811941.2 dated Aug. 3, 2018, 7 pages.
Office Action of U.S. Appl. No. 15/656,595 dated Oct. 2, 2018, 143 pages.
Office Action of U.S. Appl. No. 15/720,489 dated Oct. 1, 2018, 146 pages.

SYSTEM AND METHOD FOR DETERMINING CHANGES IN A BODY STATE

RELATED APPLICATIONS

This application is a continuation of and claims priority to U.S. patent application Ser. No. 13/843,077, filed on Mar. 15, 2013, which is expressly incorporated herein by reference.

BACKGROUND

Data related to the biological systems of an individual can indicate a body state of an individual or a transition from one body state to another body state. Exemplary biological systems can include the circulatory system, respiratory system, nervous system, including the autonomic nervous system, or other similar biological systems. Accurate and quantifiable measurements of biological systems are useful in various applications to provide feedback to the individual on their current, historical or impending body state. In particular, functional or structural variations in cardiac activity can indicate biological system activity levels (e.g., parasympathetic and sympathetic activity levels of the autonomic nervous system), which can provide accurate measurements of a body state or a transition from one body state to another body state.

SUMMARY

According to one aspect, a computer-implemented method for determining changes in a body state of an individual includes receiving a signal from a monitoring system where the signal indicates a measurement of cardiac activity of the individual over a period of time. The method also includes determining at least one signal feature, where the signal feature is a reoccurring event of the signal over the period of time. The method further includes determining a first interval between two successive signal features and determining a second interval between two successive first intervals. A derivative is calculated based on the second interval and changes in the body state are identified based on the derivative.

According to another aspect, a computer-implemented method for analyzing transitions in a body state includes receiving a signal from an individual indicating a measurement of cardiac activity over a period of time and calculating a derivative of a heart rate based on a reoccurring feature of the signal. The method further includes extracting a plurality of heart rate accelerations or decelerations based on the derivative and identifying a transition in the body state based on the plurality of heart rate accelerations or decelerations.

According to a further aspect, a computer system for determining changes in a body state of an individual includes a monitoring system configured to monitor cardiac activity and a signal receiving module configured to receive a signal from the monitoring system, where the signal represents a measurement of cardiac activity. The system also includes a feature determination module configured to determine a signal feature, where the signal feature is a reoccurring event of said signal over the period of time. The system also includes an interval determination module configured to determine a first interval between two successive signal features and a second interval between two successive first intervals. The system further includes a derivative calculation module configured to calculate a derivative of a heart rate based on the second interval and an identification module configured to identify changes in the body state based on the derivative.

According to another aspect, a non-transitory computer-readable medium storing computer-executable instructions that when executed by a computer, which includes at least a processor, cause the computer to perform a method, the method includes receiving, using at least the processor, a signal indicating a measurement of cardiac activity over a period of time. The method also includes detecting, using at least the processor, a signal feature, wherein the signal feature is a reoccurring event of the signal over the period of time and calculating, using at least the processor, a first interval between two successive signal features. The method further includes calculating, using at least the processor, a second interval between two successive first intervals and calculating, using at least the processor, a derivative based on the second interval. Finally, the method includes identifying, using at least a processor, changes in a body state based on the derivative.

DETAILED DESCRIPTION

Figure 1:
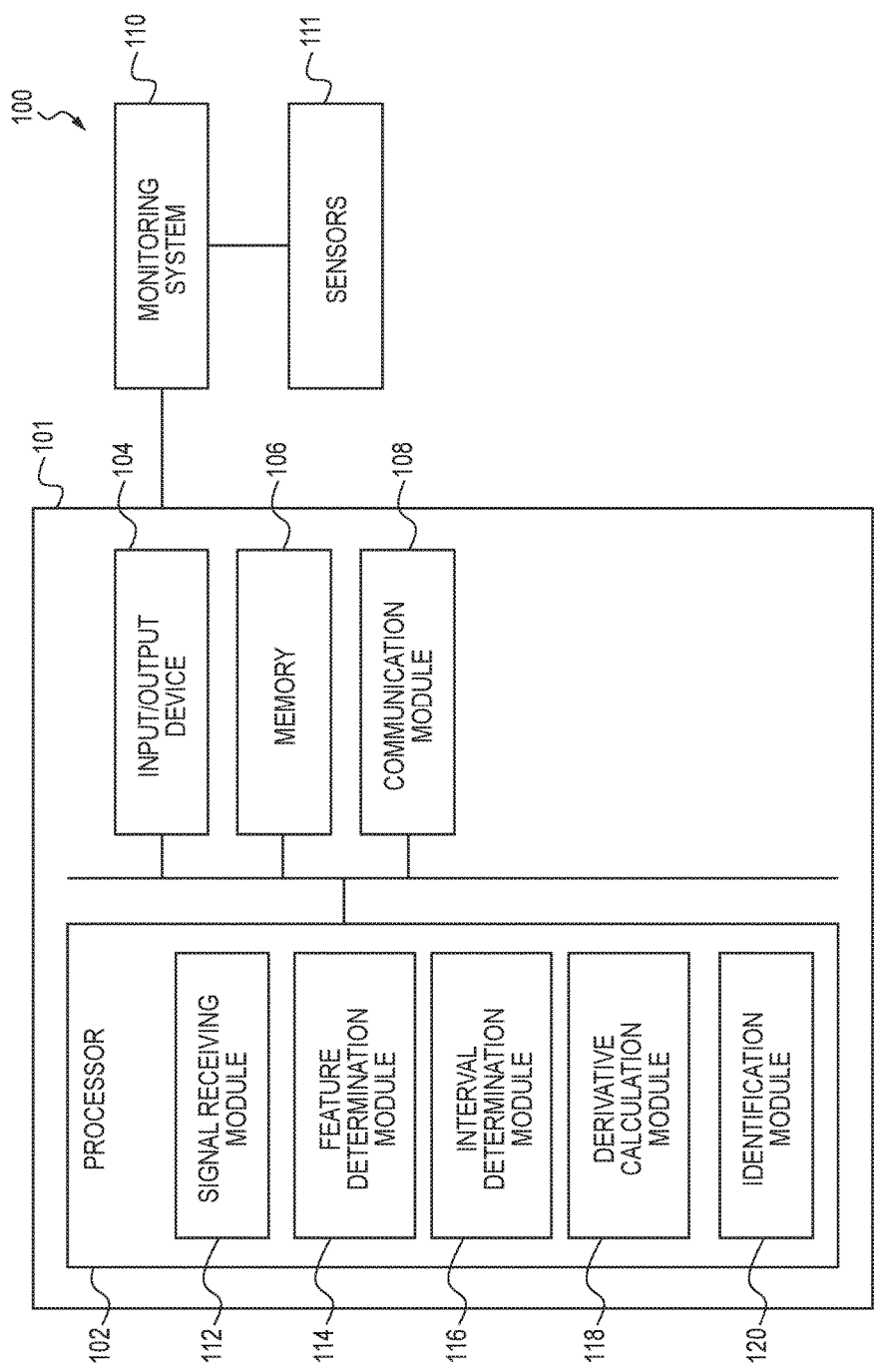
FIG. 1 is a schematic view of an illustrative computer system for determining changes in a body state according to an exemplary embodiment.

Referring now to the drawings, wherein the showings are for purposes of illustrating one or more exemplary embodiments and not for purposes of limiting same, FIG. 1 illustrates a computer system 100 in which one or more embodiments discussed herein can operate. The computer system 100 includes a computing device 101, a processor 102, an input/output device 104, a memory 106, a communication module 108 and a monitoring system 110. The monitoring system 110 can include and/or communicate with a plurality of sensors 111. In some embodiments, one or more of the components in the computer system 100 may be combined, omitted or organized into different architectures. For example, the input/output device 104 can be organized into separate input and output devices, the memory 106 can be included with the processor 102 and so forth.

It is to be appreciated, that other components not shown in FIG. 1 can be included (e.g., communication units/gateways, network buses, vehicle systems (see FIG. 2)). Additionally, although the aforementioned components, systems and methods are referred to herein with reference to system 100 and FIG. 1, it is to be appreciated that the components can be associated with or incorporated into other devices. Other exemplary devices may include, but are not limited to, clothes, jewelry or other wearable devices, seats, chairs, beds, benches, couches, or other seating devices, automobiles, trucks, motorcycles, tractor trailers, tractors, lawn mowers, airplanes, boats, and other vehicles.

Figure 2:
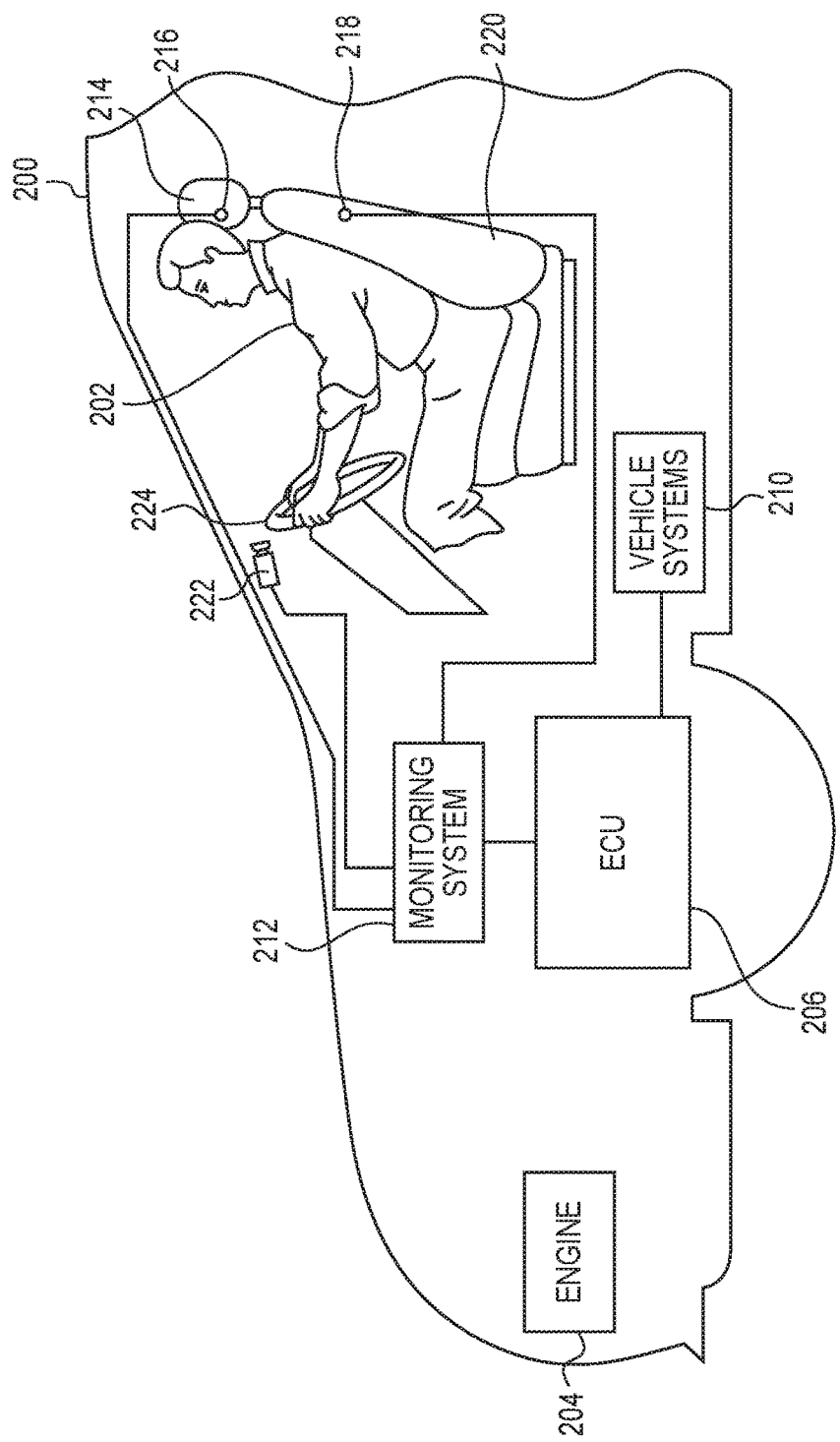
FIG. 2 is a schematic view of a motor vehicle for determining changes in a body state according to the exemplary embodiment of FIG. 1.

One exemplary embodiment is illustrated in FIG. 2, a motor vehicle 200 for determining changes in a body state of a vehicle occupant 202. The vehicle 200 can refer to any moving vehicle that is capable of carrying one or more human occupants and powered by a form of energy. The vehicle 200 includes an engine 204, an electronic control unit (ECU) 206, a plurality of vehicle systems 210 and a monitoring system 212. The monitoring system 212 can be the same or similar to the monitoring system 110. For example, the monitoring system 212 can include and/or communicate with various sensors. Specifically, in FIG. 2, the sensors include a first sensor 216 in a headrest 214, a second sensor 218 in a seat 220 and a camera 222. A steering wheel 224 may also include sensors (not shown) for identifying body state changes. Exemplary vehicle systems 210 can include, but are not limited to, an electronic stability control system, an anti-lock brake system, a brake assist system, an automatic brake prefill system, a low speed follow system, a cruise control system, a collision warning system, a collision mitigation braking system, an auto cruise control system, a lane departure warning system, a blind spot indicator system, a lane keep assist system, a navigation system, an electronic power steering system, a climate control system, an infotainment system including visual devices, audio devices and tactile devices, among others.

The components of the system 100, in whole or in part, can be integrated or associated with the vehicle 200. For example, components of the computing device 102 can be integrated with the ECU 206 located inside the vehicle 200. Similar to the device 101 of FIG. 1, the ECU 206 includes provisions for general computing and arithmetic functions as well as provisions for communicating and/or controlling various systems associated with the vehicle 200, the engine 204, the plurality of vehicle systems 210, and the monitoring system 212.

Referring again to FIG. 1, the processor 102 processes signals and performs general computing and arithmetic functions. Signals processed by the processor 102 can include digital signals, data signals, computer instructions, processor instructions, messages, a bit, a bit stream, or other means that can be received, transmitted and/or detected. In particular, the processor 102 is configured to transmit, receive and process signals from the input/output device 104, the memory 106, the communication module 108 and the monitoring system 110. Generally, the processor 102 can be a variety of various processors including multiple single and multicore processors and co-processors and other multiple single and multicore processor and co-processor architectures.

Further, the processor 102 includes a signal receiving module 112, a feature determination module 114, an interval determination module 116, a derivative calculation module 118 and an identification module 120, which process data signals and execute functions as described in further detail herein. Module, as used herein, includes, but is not limited to, hardware, firmware, software in execution on a machine, and/or combinations of each to perform a function(s) or an action(s), and/or to cause a function or action from another module, method, and/or system. A module can include a software controlled microprocessor, a discrete logic circuit, an analog circuit, a digital circuit, a programmed logic device, a memory device containing executing instructions, and so on. A module may include one or more gates, combinations of gates, or other circuit components.

The input/output device 104 represents devices to provide input (e.g., user input) to the computer system 100 and to provide output from the computer system 100 (e.g., display images, data and other feedback, such as described herein). For example, input can be received though a cursor controller, a mouse, a keyboard, a touch screen and other mechanisms adapted to communicate information or command to the processor 102 or memory 106 through the computer system 100. Output devices can include a screen, a monitor, a touch screen, a navigation display, a portable device screen (e.g., mobile phone, laptop), any other similarly equipped display devices, etc.

The memory 106 stores instructions and/or data executed and/or processed by the processor 102. The memory can include one or more different types of memory for storing data temporarily, semi-permanently or permanently. For example, cache memory, Random Access Memory (RAM), Read-Only Memory (ROM), hard-drive, solid state drive, flash memory or any combination thereof.

The communication module 108 facilitates communication between the processor 102 and other components of computer system 100, other networks (e.g., the Internet, Wide Local Area Networks (WLAN)) and other systems, for example, the monitoring system 110. Communication can be enabled via wired, wireless or telecommunication protocol technologies known in the art. For example, communication can include a network transfer, a file transfer, an applet transfer, an email, an HTTP transfer, and so on. Communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, among others.

The monitoring system 110 is configured to monitor and measure monitoring information associated with an individual for determining changes in a body state of the individual and transmit the information to the device 101. The monitoring information as used herein can include physiological and environmental information related to the individual. Physiological information can include, but is not limited to, physical characteristics of the individual (e.g., posture, position, movement) and biological characteristics of the individual (e.g., cardiac activity, such as, heart rate, electrocardiogram (EKG), blood pressure, blood flow, oxygen content in the blood) and other biological systems of the individual (e.g., circulatory system, respiratory system, nervous system, including the autonomic nervous system, or other biological systems). Environmental information can include, but is not limited to, physical characteristics of the environment in proximity to the individual (e.g., light, temperature, weather, pressure, sounds). The monitoring system 110 can include any system configured to monitor and measure the monitoring information, such as, optical devices, thermal devices, autonomic monitoring devices (e.g., heart rate monitoring devices) as well as any other kinds of devices, sensors or systems.

In the illustrated embodiment, the monitoring system 110 includes a plurality of sensors 111 for monitoring and measuring the monitoring information. The sensors 111, as known in the art, sense a stimulus (e.g., a signal, property, measurement or quantity) using various sensor technologies and generate a data stream or signal representing the stimulus. The device 101 is capable of receiving the data stream or signal representing the stimulus directly from the sensors 111 or via the monitoring system 110. Although particular sensors are described herein, it will be appreciated by one having ordinary skill in the art that any type of suitable sensor can be utilized.

The sensors 111 can be contact sensors and/or contactless sensors and can include electric current/potential sensors (e.g., proximity, inductive, capacitive, electrostatic), subsonic, sonic, and ultrasonic sensors, vibration sensors (e.g., piezoelectric) visual, photoelectric or oxygen sensors, among others. Generally, the sensors 111 can be located in any position proximate to the individual or on the individual, in a monitoring device, such as a heart rate monitor, in a portable device, such as, a mobile device, a laptop or similar devices. The sensors and processing of signals generated by the sensors will be discussed in more detail with reference to FIG. 3 below.

Further, the monitoring system 110 and/or the device 101 can receive the monitoring information from the portable device or any other device (e.g., a watch, a piece of jewelry, clothing articles) with computing functionality (e.g., including a processor similar to processor 102). The portable device may also contain stored monitoring information or provide access to stored monitoring information on the Internet, other networks and/or external databases.

In one embodiment, illustrated in FIG. 2, the monitoring system 212 can monitor and measure monitoring information associated with the occupant 202 for determining changes in a body state of the occupant 202 and transmit the monitoring information to the ECU 206. The monitoring system 212 receives the monitoring information from various sensors. The sensors can include the sensors 216, 218 and the camera 222. Generally, the sensors could be disposed in any portion of the motor vehicle 200, for example, in a location proximate to the occupant 202. For example, the sensor 216 is located in the headrest 214. In another embodiment, the sensor 218 is located in the seat 220. In a further embodiment, a sensor (not shown) could be located on or in the steering wheel 224. In other embodiments, however, the sensors could be located in any other portion of motor vehicle 200, including, but not limited to: an armrest, dashboard, rear-view mirror as well as any other location. Moreover, in some cases, the sensor can be a portable sensor that is worn by the occupant 202, associated with a portable device located in proximity to the occupant 202, such as a smart phone or similar device, or associated with an article of clothing worn by the occupant 202.

In some embodiments, the monitoring system 212 can also measure and monitor vehicle operation data from the vehicle systems 210, sensors associated with the vehicle systems 210 or from a vehicle bus (not shown). Vehicle operation data is data related to vehicle systems and components and other types of data related to the operation and status of vehicle systems and components. Exemplary vehicle operation data can include, but is not limited to, vehicle speed, braking data, steering angles, steering torque, rotational speed, motor speed, wheel speed, vehicle location (e.g., GPS data, navigation system data) or vehicle diagnostic data.

Figure 3:
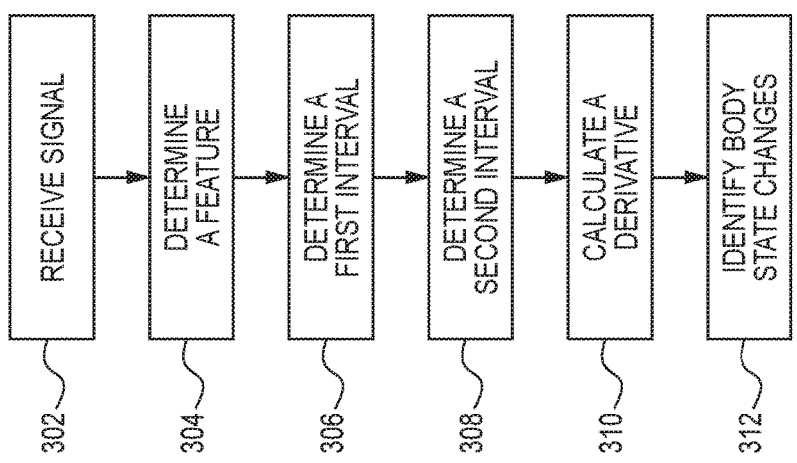
FIG. 3 is a process flow diagram of a method for determining changes in a body state.

With reference to FIG. 3, a computer implemented method is shown for determining changes in a body state of an individual. In particular, the method will be described in association with the computer system 100, though it is to be appreciated that the method could be used with other computer systems. Additionally, the method can be modified for alternative embodiments described herein (e.g., the vehicle 200, FIG. 2). It is to be appreciated that a body state herein refers to biological or physiological state of an individual or a transition to another state. For example a body state can be one or more of alert, drowsy, distracted, stressed, intoxicated, other generally impaired states, other emotional states and/or general health states. Further, cardiac activity or a measurement of cardiac activity, as used herein, refers to events related to the flow of blood, the pressure of blood, the sounds and/or the tactile palpations that occur from the beginning of one heart beat to the beginning of the next heart beat or the electrical activity of the heart (e.g., EKG). Thus, the measurement of cardiac activity can indicate a plurality of cardiac cycles or a plurality of heart beats over a period of time.

At step 302, the method includes receiving a signal from a monitoring system. The signal indicates a measurement of cardiac activity of the individual over a period of time. In one embodiment, the monitoring system 110 is configured to monitor cardiac activity of an individual from the plurality of sensors 111. As discussed above, the sensors 111, as known in the art, sense a stimulus (e.g., a signal, property, measurement or quantity) using various sensor technologies and generate a data stream or signal representing the stimulus. Specifically, the data stream or signal representing the stimulus is transmitted from the sensors to the signal receiving module 112, directly or via the monitoring system 110. In the illustrated embodiment, the signal receiving module 112 can be further configured to process the signal thereby generating a proxy of the signal in a particular form. It is appreciated that the sensors 111 or the monitoring system 110 can also perform processing functions. Processing can include amplification, mixing and filtering of the signal as well as other signal processing techniques known in the art. In one embodiment, upon receiving the signal, the signal is processed into a plurality of waveforms, where each one of the wave forms indicates one heart beat.

Particular sensors will now be described in operation for sensing monitoring information, specifically, physiological characteristics (e.g., cardiac activity). Although specific sensors and methods of sensing are discussed herein, it will be appreciated that other sensors and methods of sensing cardiac activity can be implemented. The sensors 111 can be contact sensors and/or contactless sensors and can include electric current/potential sensors (e.g., proximity, inductive, capacitive, electrostatic), subsonic, sonic, and ultrasonic sensors, vibration sensors (e.g., piezoelectric), visual, photoelectric or oxygen sensors, among others.

Electric current/potential sensors are configured to measure an amount or change in an electric current, electrical charge or an electric field. In one embodiment, electric potential sensors can measure electrical activity of the heart of the individual over a period of time (i.e., an EKG). The electric potential sensors can be contact sensors or contactless sensors located on or in proximity to the individual. For example, in the embodiment illustrated in FIG. 2, the first sensor 216 and/or the second sensor 218 and/or the third sensor (not shown) disposed in the steering wheel 224 could be electric potential sensors.

Sonic sensors are configured to measure sound waves or vibration at frequencies below human auditory range (subsonic), at frequencies within human auditory range (sonic) or at frequencies above human auditory range (ultrasonic). In one embodiment, sonic sensors can measure sound waves or vibration generated by cardiac activity. In another embodiment, ultrasonic sensors generate high frequency sound waves and evaluate the echo received back by the sensor. Specifically, ultrasonic sensors can measure sounds or vibrations produced by the heart. For example, the ultrasonic sensors can generate sound waves towards the thoracic region (e.g., in front or back of chest area) of an individual and measure an echo received back by the sensor indicating cardiac activity.

Visual sensors provide image-based feedback and include machine vision systems, cameras and other optical sensors. Digital signals generated by the visual sensors include a sequence of images to be analyzed. For example, in one embodiment, a camera (e.g., the camera 222, FIG. 2) can generate images of eye movement, facial expressions, positioning or posture of the individual.

Figure 6:
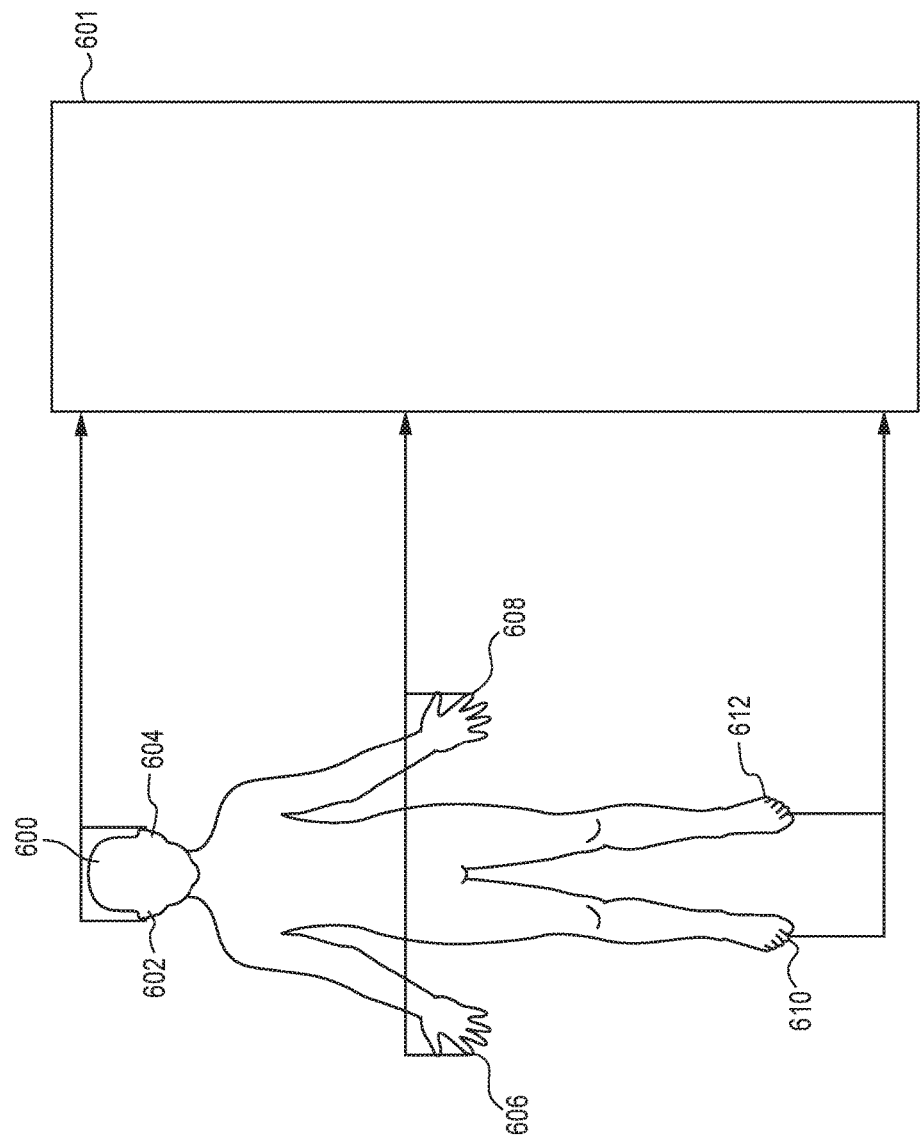
FIG. 6 is a schematic view of locations on an individual for measuring cardiac activity.

Photoelectric sensors use optics and light (e.g., infrared) to detect a presence, a volume or a distance of an object. In one embodiment, the photoelectric sensors optically obtain a photoplethysmogram (PPG) of cardiac activity, which is a volumetric measurement of pulsatile blood flow. PPG measurements can be sensed at various locations on or near an individual's body using, for example, a pulse oximeter. FIG. 6 illustrates a schematic representation of an individual 600 and a PPG analysis computer 601. PPG measurements can be obtained from different locations of the individual 600, for example, a left ear 602, a right ear 604, a left hand/finger 606, a right hand/finger 608, a left foot/toe 610 and a right foot/toe 612. The measurements can be obtained by photoelectric sensors near or on the above mentioned locations and transmitted to the PPG analysis computer 601. The PPG analysis computer 601 includes provisions for analyzing the PPG measurements and comparing PPG measurements obtained from different locations of the individual 600. In some embodiments, the monitoring system 111 or the processor 102 of FIG. 1 can perform the functions of the PPG analysis computer 601.

Referring again to FIG. 3, at step 304, the method includes determining at least one signal feature, wherein the signal feature is a reoccurring event over the period of time. In one embodiment, the feature determination module 114 receives the signal from the signal receiving module 112 and determines the signal feature. The signal feature can be a signal or signal waveform (i.e., shape) characteristic. Exemplary signal features include, but are not limited to, a deflection, a sound, a wave, a duration, an interval, an amplitude, a peak, a pulse, a wavelength or a frequency that reoccurs in the signal over the period of time.

As discussed above, the sensors 111 generate a signal representing the stimulus measured. The signal and the signal features vary depending on the property (i.e., the physiological, biological or environmental characteristic) sensed, the type of sensor and the sensor technology. The following are exemplary cardiac waveforms (i.e., signals indicating a measurement of cardiac activity) with signal features reoccurring over a period of time. Although specific waveforms are disclosed with respect to cardiac activity, it will become apparent to one having ordinary skill in the art that the methods and systems disclosed herein, are applicable to waveforms and signals associated with other physiological or environment characteristics associated with individual for identifying a body state or a transition to a body state.

Figure 4A:
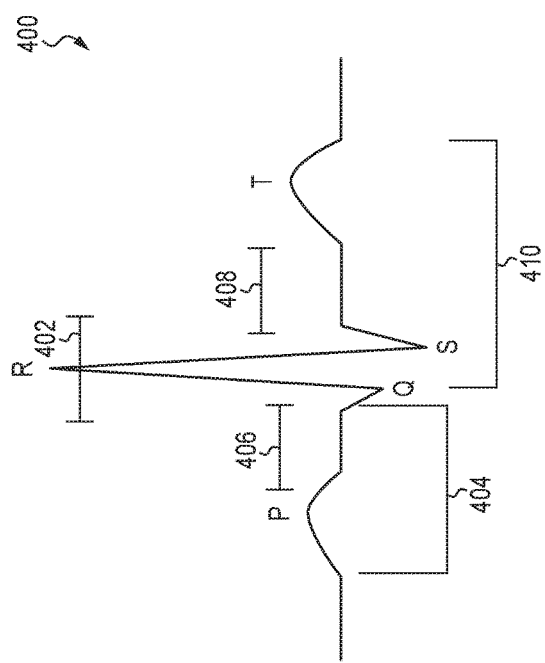
FIG. 4(a) is a schematic representation of a cardiac waveform of an electrical signal representing cardiac activity.
Figure 4B:
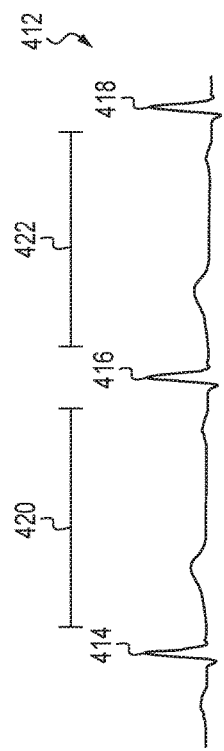
FIG. 4(b) is a schematic representation of a series of cardiac waveforms of FIG. 4(a)

Referring now to FIG. 4(a), a cardiac waveform 400 of an electrical signal representing cardiac activity is illustrated. In particular, the cardiac waveform 400 represents an EKG waveform 400, which is a graphical representation of the electrical activity of a heart beat (i.e., one cardiac cycle). As is known in the art, and as shown in FIGS. 4(b) (i.e., a series of cardiac waveforms 412) and 7, it is to be appreciated that an EKG can include a plot of the variation of the electrical activity over a period of time (i.e., multiple cardiac cycles).

Figure 7:
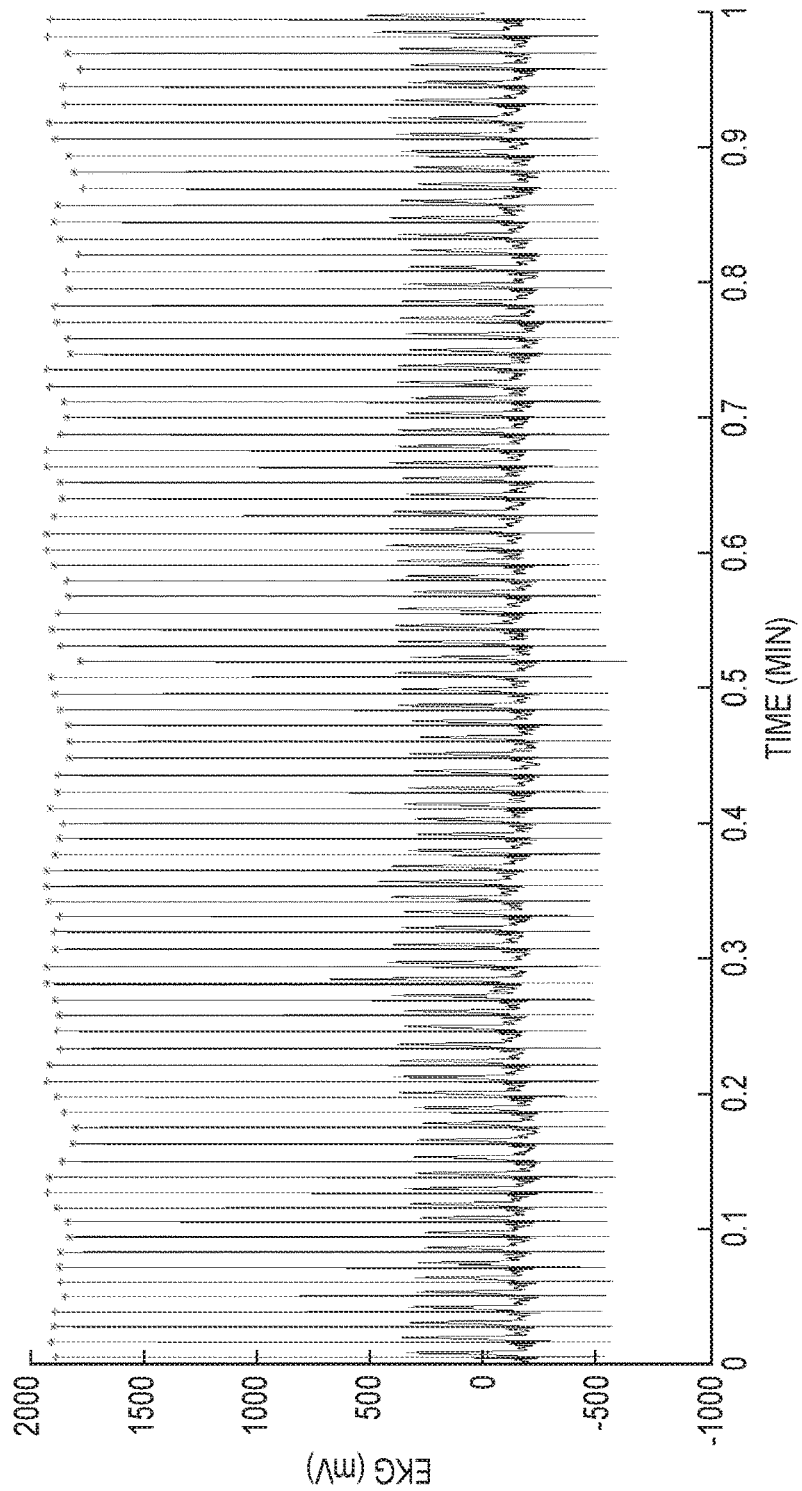
FIG. 7 is an example output of a single lead electrocardiogram (EKG)

Each portion of a heartbeat produces a different deflection on the EKG waveform 400. These deflections are recorded as a series of positive and negative waves, namely, waves P, Q, R, S and T. The Q, R and S waves comprise a QRS complex 402 which indicates rapid depolarization of the right and left heart ventricles. The P wave indicates atrial depolarization and the T wave indicates atrial repolarization. Each wave can vary in duration, amplitude and form in different individuals. In FIG. 4(b) the R waves are indicated by the peaks 414, 416 and 418. In FIG. 7, the R wave of each heartbeat is indicated with an asterisk (*). In a normal EKG, the R wave can be the peak of the QRS complex 402.

Other signal features include wave durations or intervals, namely, PR interval 404, PR segment 406, ST segment 408 and ST interval 410. The PR interval 404 is measured from the beginning of the P wave to the beginning of the QRS complex 402. The PR segment 406 connects the P wave and the QRS complex 402. The ST segment 408 connects the QRS complex and the T wave. The ST interval 410 is measured from the S wave to the T wave. It is to be appreciated that other intervals (e.g., QT interval) can be identified from the EKG waveform 400. Additionally, beat-to-beat intervals (i.e., intervals from one cycle feature to the next cycle feature), for example, an R-R interval (i.e., the interval between an R wave and the next R wave), may also be identified.

With reference to the method of FIG. 3, in one embodiment, determining a signal feature includes determining the signal feature as an R wave of an EKG signal. For example, the R wave of the EKG waveform 400. It is appreciated that the signal feature could also be one or more waves P, Q, R, S and T or one or more of the intervals described above.

Figure 5B:
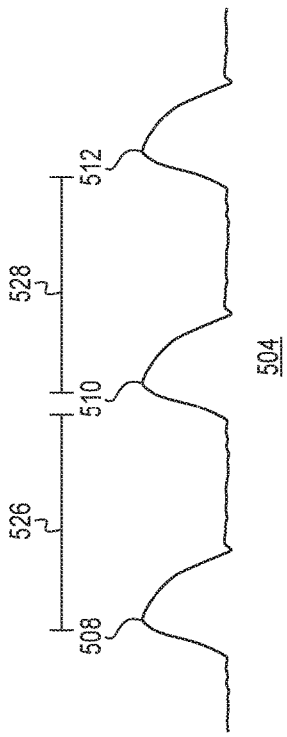
FIG. 5(b) is a schematic representation of a series of cardiac waveforms of FIG. 5(a)
Figure 5D:
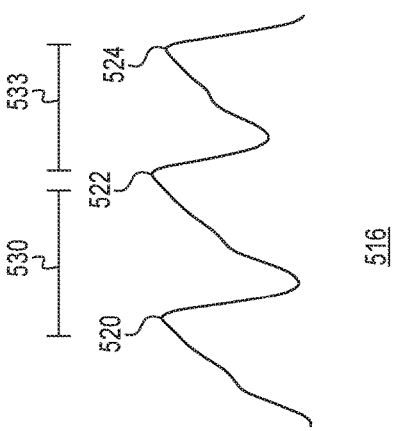
FIG. 5(d) is a schematic representation of a series of cardiac waveforms of FIG. 5(c)
Figure 5A:
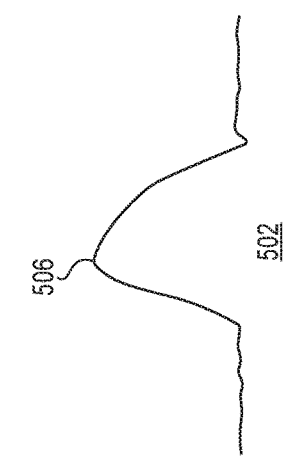
FIG. 5(a) is a schematic representation of a cardiac waveform of an acoustic signal representing cardiac activity.

FIG. 5(a) illustrates another embodiment of a cardiac waveform 502 of an acoustic signal representing cardiac activity generated or processed from a sensor, for example, a sonic or vibrational sensor. In particular, the cardiac waveform 502 represents the sound of aortic blood flow. The cardiac waveform 502 can include signal features similar to the cardiac waveform 400. Exemplary signal features can include a peak 506 or another wave duration, peak, feature of the waveform 502. Specifically, the signal feature reoccurs in the signal over a period of time. For example, FIG. 5(b) illustrates an acoustic signal 504 having a series of cardiac waveforms (i.e., the cardiac waveform 502) with a series of peaks 508, 510, 512. The peaks 508, 510, 512 are an exemplary signal feature that reoccurs in the acoustic signal 504 over a period of time. It is appreciated that other characteristics of the waveform 502 and/or the signal 504 can also be identified as a signal feature.

Figure 5C:
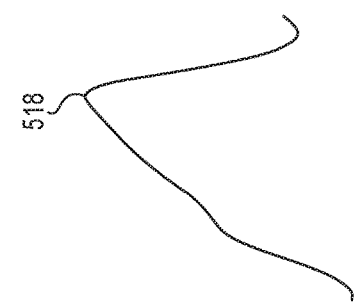
FIG. 5(c) is a schematic representation of a cardiac waveform of an optical signal representing cardiac activity.

FIG. 5(c) illustrates a cardiac waveform 514 from an optical signal representing a measurement of cardiac activity. The optical signal can be a photoplethsymograph (PPG) signal generated from a photoelectric sensor or a PPG device. The cardiac waveform 514 is a PPG signal representing a measurement of pulsatile blood flow. The cardiac waveform 514 can include signal features similar to the cardiac waveform 400. Exemplary signal features can include a peak 518 or another wave duration, peak, feature of the waveform 514. Specifically, the signal feature reoccurs in the signal over a period of time. For example, FIG. 5(*d*) illustrates an optical signal 516 having a series of cardiac waveforms (i.e., the cardiac waveform 514) with a series of peaks 520, 522, 524. The peaks 520, 522, 524 are an exemplary signal feature that reoccurs in the optical signal 516 over a period of time. It is appreciated that other characteristics of the waveform 514 and/or the signal 516 can also be identified as a signal feature.

Referring back to step 304, determining at least one signal feature may include determining a time occurrence of the signal feature. The time occurrence of each signal feature in the signal may be stored in a memory 106 as a vector. For example, the time occurrence of each R wave of the EKG signal may be stored and expressed in vector form as:

$T_{0,i} = t_{0,0}, t_{0,1} \ldots t_{0,i}$ where $t_{0,i}$ is the time of observance of the R wave component of the QRS complex and $0 \leq i \leq N$. (a)

For simplicity, the expressions (a)-(d) discussed herein are with reference to the R wave of the cardiac waveform 400 (EKG waveform) as a signal feature. It is to be appreciated that the signal feature could be any signal feature identified in other types of signals as discussed above. For example, $t_{0,i}$ could also indicate a time observance of a peak 506 of a cardiac waveform 502 or a peak 518 or a cardiac waveform 514. It is also appreciated that each expression may contain multiple elements of calculations derived from a signal. The elements can be stored, for example in a memory 106, in vector form.

At step 306, the method includes determining a first interval between two successive signal features. In another embodiment, a first interval is an interval between two successive features of each one of the heart beats of the signal. Successive features, as used herein, is used to refer to signal features that follow each other or are produced in succession. For example, a first interval can be an interval between a first R wave and a second R wave of the EKG signal (i.e., R-R interval), where the second R wave is the next successive R wave to the first R wave. With reference to FIG. 4(*b*), a first interval can be an interval 420 measured from the peak 414 and to the peak 416. A first interval can also be an interval 422 measured from the peak 416 to the peak 418. Thus, it is appreciated that a signal can include a plurality of first intervals between a plurality of signal features. In another example shown in FIG. 5(*b*), a first interval can be an interval 526 measured from the peak 508 to the peak 510. A first interval can also be an interval 528 measured from the peak 510 to the peak 512. In another example shown in FIG. 5(*d*), a first interval can be an interval 530 measured from the peak 520 to the peak 522. A first interval can also be an interval 533 measured from the peak 522 and to the peak 524. With respect to the expressions (a)-(b), a plurality of first intervals for an EKG signal can be expressed in vector form as:

$T_{1,i} = t_{1,1}, t_{1,2} \ldots t_{1,i}$ where $t_{1,i} \equiv t_{0,i} - t_{0,i-1}$ and $1 \leq i \leq N$. (b)

At step 308, the method includes determining a second interval between two successive first intervals. In one embodiment, the interval determination module 116 can determine the first interval and the second interval. In one example, the second interval is an interval, or a difference, between successive R-R intervals. For example, a second interval can be the difference between the absolute value of a first R-R interval and the absolute value of a second R-R interval, where the second R-R interval is the next successive R-R interval to the first R-R interval. With reference to FIG. 4(*b*), the second interval can be a difference between the interval 420 and the interval 422. In another example shown in FIG. 5(*b*), the second interval can be a difference between the interval 526 and the interval 528. In a further example shown in FIG. 5(*d*), the second interval can be a difference between the interval 530 and the interval 533. It is understood that a signal can include a plurality of second intervals defined by a plurality of first intervals. With respect to expressions (a)-(b), this difference can be expressed in vector form as:

$T_{2,i} = t_{2,2}, t_{2,3} \ldots t_{2,i}$ where $t_{2,i} \equiv \lfloor t_{1,i} \rfloor - \lfloor t_{1,i-1} \rfloor$ and $2 \leq i \leq N$. (c)

At step 310 the method includes calculating a derivative based on the second interval. In one embodiment, the derivative calculation module 118 is configured to calculate the derivative. The derivative can be calculated as the second interval divided by the period of time. With respect to expressions (a)-(c), the derivative can be expressed in vector form as:

$$T_{3,i} = t_{3,2}, t_{3,3} \ldots t_{3,i} \text{ where } t_{3,i} \equiv \frac{t_{2,i}}{t_{0,i} - t_{0,i-2}} \text{ and } 2 \leq i \leq N. \quad (d)$$

At step 312, the method includes identifying changes in the body state based on the derivative. The identification module 122 can be configured to manipulate the data from expressions (a)-(d) in various ways to identify patterns and metrics associated with the body state. In one embodiment, identifying the changes in the body state further includes extracting a series of contiguous heart rate accelerations or decelerations based on the derivative. For example, Table 1, shown below, is populated with data from expressions (a)-(d). Heart rate acceleration or decelerations can be extracted from Table 1.

TABLE 1

Derivation of the first derivative of heart rate

| i | $T_0$ | $T_1$ | $T_2$ | $T_3$ |
|---|---|---|---|---|
| 0 | $t_0$ | NA | NA | |
| 1 | $t_1$ | $t_1 - t_0$ | NA | |
| 2 | $t_2$ | $t_2 - t_1$ | $\lvert t_2 - t_1 \rvert - \lvert t_1 - t_0 \rvert$ | $\dfrac{\lvert t_2 - t_1 \rvert - \lvert t_1 - t_0 \rvert}{t_2 - t_0}$ |
| 3 | $t_3$ | $t_3 - t_2$ | $\lvert t_3 - t_2 \rvert - \lvert t_2 - t_1 \rvert$ | $\dfrac{\lvert t_3 - t_2 \rvert - \lvert t_2 - t_1 \rvert}{t_3 - t_1}$ |
| … | … | … | … | … |

More specifically, the data from Table 1 can be sorted and flagged according to the sign of the derivative ($T_3$) of the heart rate. The sign of the derivative indicates whether the heart rate is accelerating or decelerating. Where the sign of the derivative is the same for a given number of successive derivatives ($T_3$), contiguous periods of heart rate acceleration or deceleration can be identified. The contiguous periods of heart rate acceleration or deceleration can correlate to a change in a body state. In particular a series of contiguous heart rate accelerations and a series of contiguous heart rate decelerations correlate to bursts of sympathetic (S) and parasympathetic (PS) activity respectively. Thus, by sorting and flagging contiguous time periods of heart rate acceleration and deceleration, body state changes associated with bursts of S and PS activity can be identified.

In another embodiment, identifying changes in the body state further includes calculating a threshold based on a count of the contiguous heart rate accelerations or decelerations in a particular series. For example, a threshold of 7 is associated with 7 contiguous heart rate accelerations or decelerations. Table 2, shown below, is a table of thresholds extracted and flagged from Table 1.

in $T_3$ produces considerable modulation between the first body state and the second body state. Therefore, higher thresholds (i.e., longer periods of contiguous acceleration or deceleration) correlates with prominent occurrences of sustained S and PS activity which can be indicative of a change in a body state.

In another embodiment, identifying a transition in a body state further includes generating a graphic representation illustrating at least one set of contiguous derivatives having the same sign, where the set of contiguous derivatives indicates a transition in the body state. It is appreciated that the graphical representation can also illustrate more than one

TABLE 2

Thresholds

| i | $T_0$ | $T_1$ | $T_2$ | $T_3$ | Sign $T_3$ | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| 0 | $t_0$ | NA | NA | NA | NA | NA | NA | NA | NA | NA | NA | NA | NA | NA | NA | NA | NA | NA |
| 1 | $t_1$ | $t_{1,1}$ | NA | NA | NA | NA | NA | NA | NA | NA | NA | NA | NA | NA | NA | NA | NA | NA |
| 2 | $t_2$ | $t_{1,2}$ | $t_{2,2}$ | $t_{3,2}$ | 1 | + | − | − | − | − | − | − | − | − | − | − | − | − |
| 3 | $t_3$ | $t_{1,3}$ | $t_{2,3}$ | $t_{3,3}$ | 1 | + | − | − | − | − | − | − | − | − | − | − | − | − |
| 4 | $t_4$ | $t_{1,4}$ | $t_{2,4}$ | $t_{3,4}$ | −1 | + | − | − | − | − | − | − | − | − | − | − | − | − |
| 5 | $t_5$ | $t_{1,5}$ | $t_{2,5}$ | $t_{3,5}$ | −1 | + | − | − | − | − | − | − | − | − | − | − | − | − |
| 6 | $t_6$ | $t_{1,6}$ | $t_{2,6}$ | $t_{3,6}$ | 1 | − | − | − | − | − | − | − | − | − | − | − | − | − |
| 7 | $t_7$ | $t_{1,7}$ | $t_{2,7}$ | $t_{3,7}$ | −1 | − | − | − | − | − | − | − | − | − | − | − | − | − |
| 8 | $t_8$ | $t_{1,8}$ | $t_{2,8}$ | $t_{3,8}$ | 1 | − | − | − | − | − | − | − | − | − | − | − | − | − |
| 9 | $t_9$ | $t_{1,9}$ | $t_{2,9}$ | $t_{3,9}$ | −1 | + | + | − | − | − | − | − | − | − | − | − | − | − |
| 10 | $t_{10}$ | $t_{1,10}$ | $t_{2,10}$ | $t_{3,10}$ | −1 | + | + | − | − | − | − | − | − | − | − | − | − | − |
| 11 | $t_{11}$ | $t_{1,11}$ | $t_{2,11}$ | $t_{3,11}$ | −1 | + | + | − | − | − | − | − | − | − | − | − | − | − |
| 12 | $t_{12}$ | $t_{1,12}$ | $t_{2,12}$ | $t_{3,12}$ | 1 | + | + | − | − | − | − | − | − | − | − | − | − | − |
| 13 | $t_{13}$ | $t_{1,13}$ | $t_{2,13}$ | $t_{3,13}$ | 1 | + | + | − | − | − | − | − | − | − | − | − | − | − |
| 14 | $t_{14}$ | $t_{1,14}$ | $t_{2,14}$ | $t_{3,14}$ | 1 | + | + | − | − | − | − | − | − | − | − | − | − | − |
| 15 | $t_{15}$ | $t_{1,15}$ | $t_{2,15}$ | $t_{3,15}$ | −1 | − | − | − | − | − | − | − | − | − | − | − | − | − |
| 16 | $t_{16}$ | $t_{1,16}$ | $t_{2,16}$ | $t_{3,16}$ | 1 | + | + | + | + | + | + | + | + | + | + | + | + | + |
| 17 | $t_{17}$ | $t_{1,17}$ | $t_{2,17}$ | $t_{3,17}$ | 1 | + | + | + | + | + | + | + | + | + | + | + | + | + |
| 18 | $t_{18}$ | $t_{1,18}$ | $t_{2,18}$ | $t_{3,18}$ | 1 | + | + | + | + | + | + | + | + | + | + | + | + | + |
| 19 | $t_{19}$ | $t_{1,19}$ | $t_{2,19}$ | $t_{3,19}$ | 1 | + | + | + | + | + | + | + | + | + | + | + | + | + |
| 20 | $t_{20}$ | $t_{1,20}$ | $t_{2,20}$ | $t_{3,20}$ | 1 | + | + | + | + | + | + | + | + | + | + | + | + | + |
| 21 | $t_{21}$ | $t_{1,21}$ | $t_{2,21}$ | $t_{3,21}$ | 1 | + | + | + | + | + | + | + | + | + | + | + | + | + |
| 22 | $t_{22}$ | $t_{1,22}$ | $t_{2,22}$ | $t_{3,22}$ | 1 | + | + | + | + | + | + | + | + | + | + | + | + | + |
| 23 | $t_{23}$ | $t_{1,23}$ | $t_{2,23}$ | $t_{3,23}$ | 1 | + | + | + | + | + | + | + | + | + | + | + | + | + |
| 24 | $t_{24}$ | $t_{1,24}$ | $t_{2,24}$ | $t_{3,24}$ | 1 | + | + | + | + | + | + | + | + | + | + | + | + | + |
| 25 | $t_{25}$ | $t_{1,25}$ | $t_{2,25}$ | $t_{3,25}$ | 1 | + | + | + | + | + | + | + | + | + | + | + | + | + |
| 26 | $t_{26}$ | $t_{1,26}$ | $t_{2,26}$ | $t_{3,26}$ | 1 | + | + | + | + | + | + | + | + | + | + | + | + | + |
| 27 | $t_{27}$ | $t_{1,27}$ | $t_{2,27}$ | $t_{3,27}$ | 1 | + | + | + | + | + | + | + | + | + | + | + | + | + |
| 28 | $t_{28}$ | $t_{1,28}$ | $t_{2,28}$ | $t_{3,28}$ | 1 | + | + | + | + | + | + | + | + | + | + | + | + | + |
| 29 | $t_{29}$ | $t_{1,29}$ | $t_{2,29}$ | $t_{3,29}$ | 1 | + | + | + | + | + | + | + | + | + | + | + | + | + |
| 30 | $t_{30}$ | $t_{1,30}$ | $t_{2,30}$ | $t_{3,30}$ | −1 | + | + | + | + | + | − | − | − | − | − | − | − | − |
| 31 | $t_{31}$ | $t_{1,31}$ | $t_{2,31}$ | $t_{3,31}$ | −1 | + | + | + | + | + | − | − | − | − | − | − | − | − |
| 32 | $t_{32}$ | $t_{1,32}$ | $t_{2,32}$ | $t_{3,32}$ | −1 | + | + | + | + | + | − | − | − | − | − | − | − | − |
| 33 | $t_{33}$ | $t_{1,33}$ | $t_{2,33}$ | $t_{3,33}$ | −1 | + | + | + | + | + | − | − | − | − | − | − | − | − |
| 34 | $t_{34}$ | $t_{1,34}$ | $t_{2,34}$ | $t_{3,34}$ | −1 | + | + | + | + | + | − | − | − | − | − | − | − | − |
| 35 | $t_{35}$ | $t_{1,35}$ | $t_{2,35}$ | $t_{3,35}$ | −1 | + | + | + | + | + | − | − | − | − | − | − | − | − |
| 36 | $t_{36}$ | $t_{1,36}$ | $t_{2,36}$ | $t_{3,36}$ | 1 | − | − | − | − | − | − | − | − | − | − | − | − | − |
| 37 | $t_{37}$ | $t_{1,37}$ | $t_{2,37}$ | $t_{3,37}$ | −1 | + | − | − | − | − | − | − | − | − | − | − | − | − |
| 38 | $t_{38}$ | $t_{1,38}$ | $t_{2,38}$ | $t_{3,38}$ | −1 | + | − | − | − | − | − | − | − | − | − | − | − | − |

Figure 8:
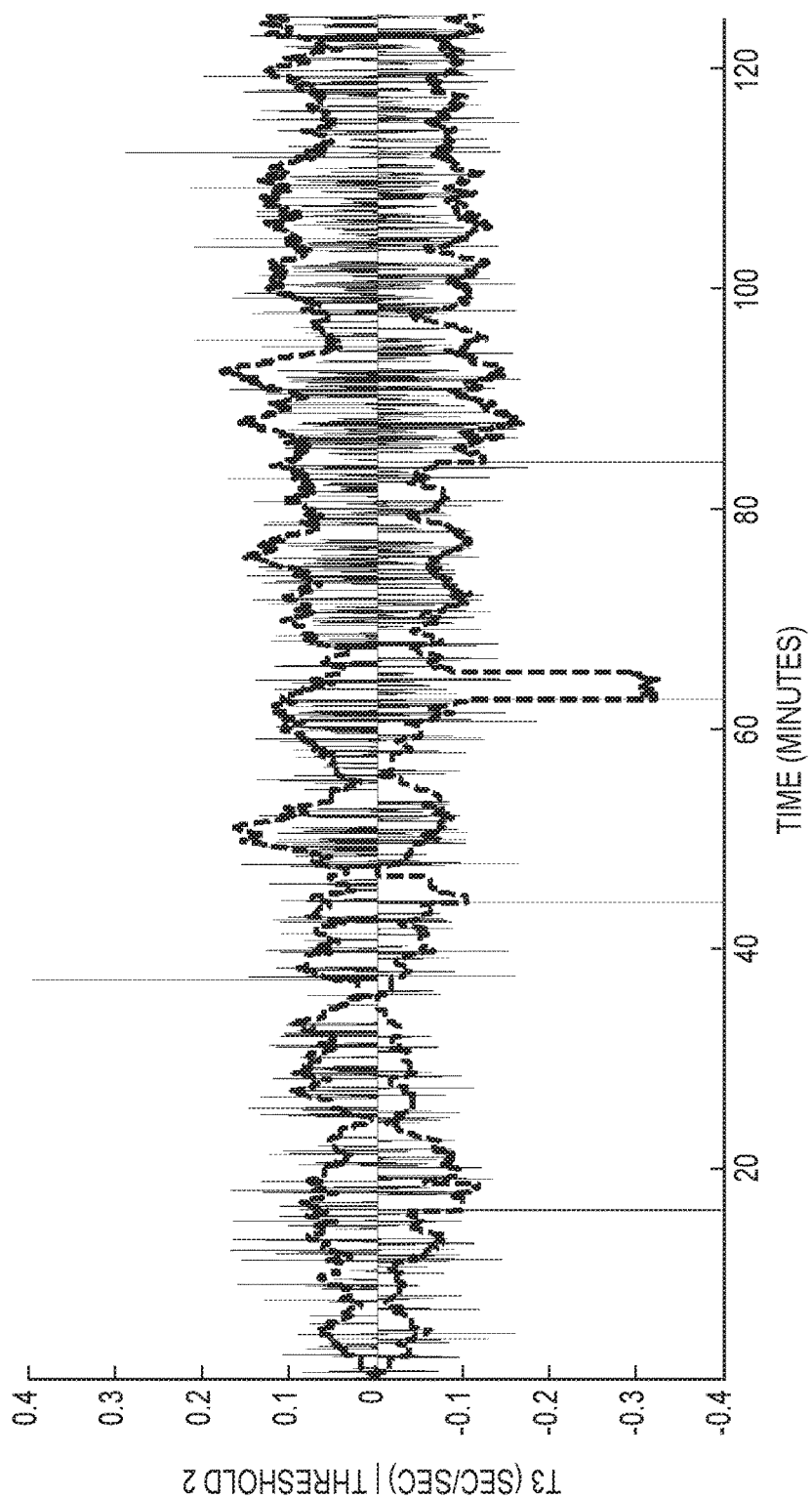
FIG. 8 is an example line plot of a derivative of a heart rate at low thresholds (i.e., 2)
Figure 9:
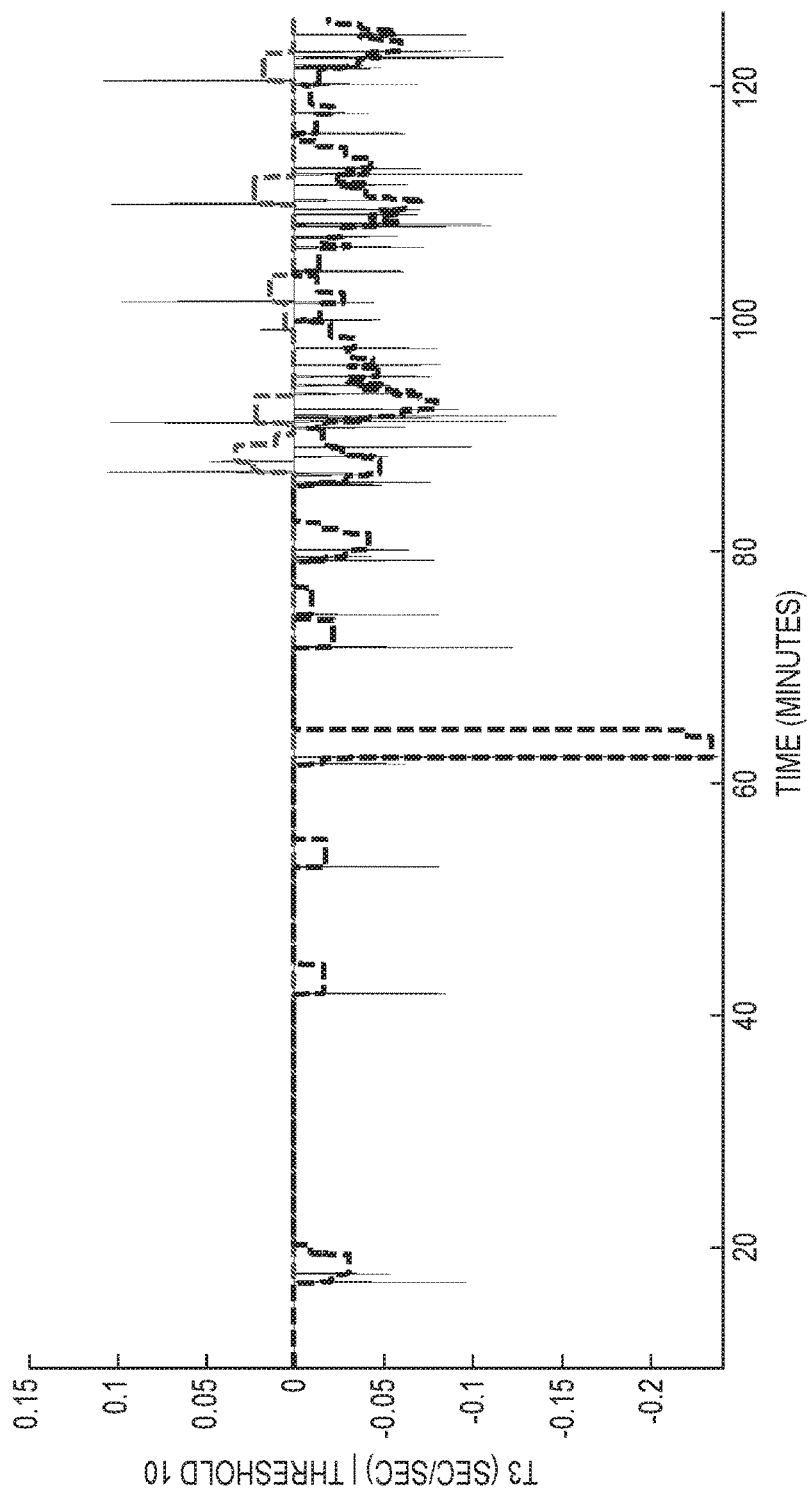
FIG. 9 is an example line plot of a derivative of a heart rate at high thresholds (i.e., 10)
Figure 10:
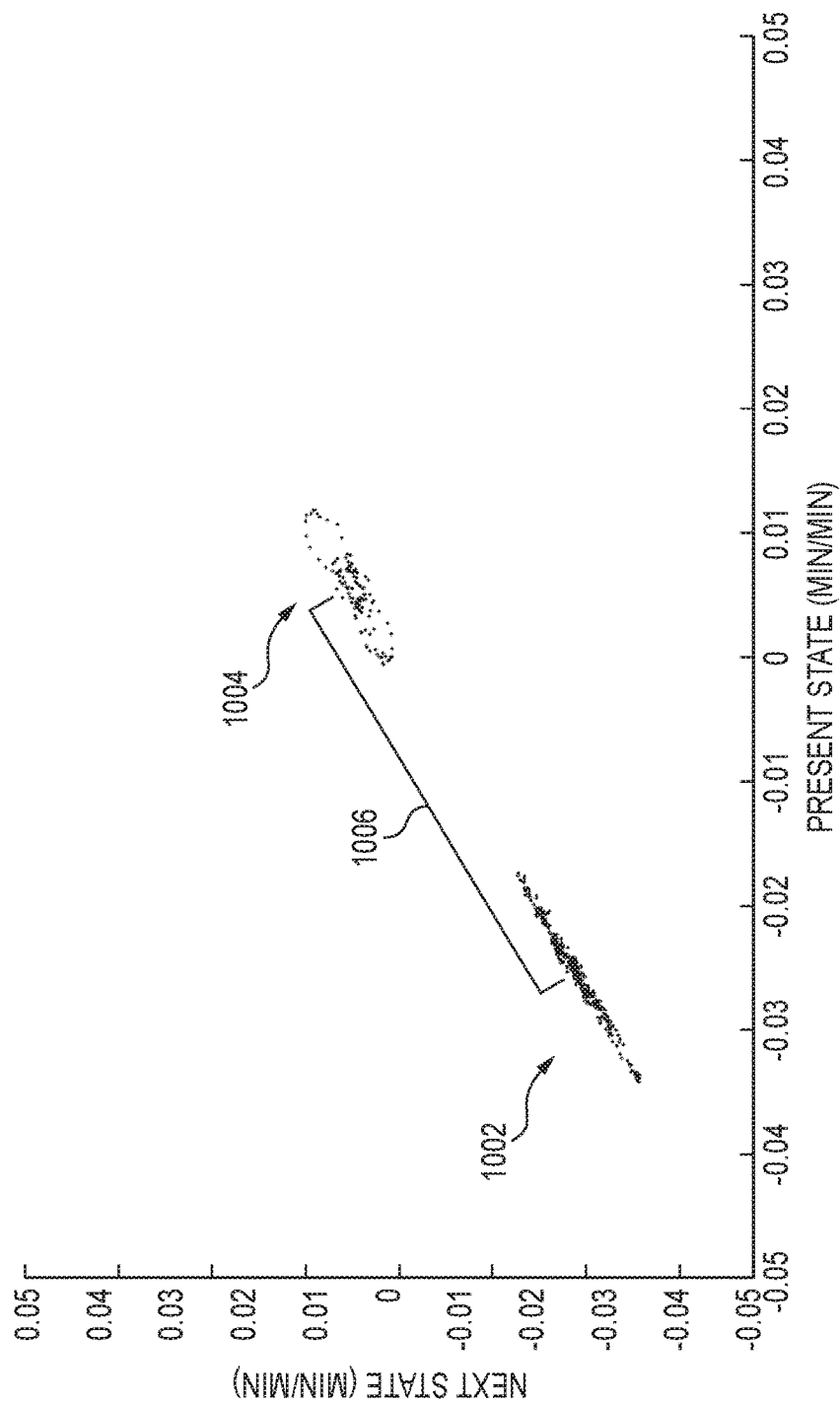
FIG. 10 is an example cluster plot of a derivative of a heart rate.

In one embodiment, the method can include generating a graphic representation of changes in a body state based on the derivatives, the thresholds and/or contiguous sets of the derivatives and the thresholds. It is appreciated that various graphic representations of the above mentioned data (e.g., expressions (a)-(d)) can be generated to facilitate identification of changes in a body state and analysis of transitions from one body state to another body state. FIGS. 8-10 illustrate non-limiting examples of said graphic representations. Specifically, FIGS. 8 illustrate a plot of the derivative T3 for each one of the cardiac cycles against a set of time intervals. In FIG. 8, at low thresholds (i.e., below 7) changes in $T_3$ do not distinguish between a first body state (t<60 minutes) and a second body state (t>60 minutes). However, as shown in FIG. 9, at high thresholds (i.e., above 7) changes set of contiguous derivatives, for example, a first set of contiguous derivatives having the same sign and a second set of contiguous derivatives having the same sign. FIG. 10 illustrates a cluster plot of contiguous accelerations 1002 (S pole) and contiguous decelerations 1004 (PS pole). The contiguous groupings are determined based on the sign of the derivative $T_3$. As a transition or change in a body state increases, the distance between the centers of the two clusters 1002, 1004 (i.e., inter-pole distance 1006) increases. In a further embodiment, a transition or a change in a body state can be determined as a function of a plurality of inter-pole distances over a period of time. It is appreciated that the graphic representations discussed here in, as well as the data contained in said graphic representations (e.g., thresholds, contiguous sets of derivatives), shown in FIGS.

8-10 can be analyzed and interpreted in other manners to identify a transition or a change in a body state.

Referring again to FIGS. 1 and 3, another embodiment includes a non-transitory computer-readable medium storing computer-executable instructions that when executed by a computer, for example, a computing device 101 which includes a processor 102, causes the computer to perform the method of FIG. 3. Computer-readable medium, as used herein, refers to a medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, a compact disc, other optical medium, a Random Access Memory (RAM), a Read Only Memory (ROM), a memory chip or card, a memory stick, and other media from which a computer, a processor or other electronic device can read.

Referring again to FIG. 3, which is described in detail above, the method includes at step 302, receiving, using at least the processor 102, a signal indicating a measurement of cardiac activity of an individual over a period of time. At step 304, the method includes detecting, using at least the processor 102, a signal feature, wherein the signal feature is a reoccurring event of the signal over a period of time. At step 306, the method further includes calculating, using at least the processor 102, a first interval between two successive signal features and at step 308, a second interval between two successive first intervals. At step 310, a derivative is calculated, using at least the processor 102, based on the second interval. At step 312, changes in a body state are identified, using at least the processor 102, based on the derivative. Identifying the changes in the body state further includes extracting a series of contiguous heart rate accelerations or decelerations based on the derivative. The series of contiguous heart rate accelerations or decelerations can correlate to changes in the body state.

It will be appreciated that various modifications of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A computer-implemented method for determining changes in a body state of an individual, comprising:
   receiving a signal from a monitoring system, the signal indicating a measurement of cardiac activity over a period of time;
   identifying a signal feature that repeats in the signal over the period of time;
   calculating a plurality of first intervals, wherein each first interval in the plurality of first intervals is calculated between successive signal features in the signal;
   calculating a plurality of second intervals, wherein each second interval in the plurality of second intervals is calculated between successive first intervals in the plurality of first intervals;
   calculating a derivative based on the plurality of second intervals; and
   identifying changes in the body state based on the derivative.

2. The computer-implemented method of claim 1, wherein the signal is measured by a contactless sensor.

3. The computer-implemented method of claim 2, wherein the signal is one of an electric signal, an acoustic or an optical signal representing the measurement of cardiac activity.

4. The computer-implemented method of claim 1, wherein the signal feature is a signal peak that repeats in the signal.

5. The computer-implemented method of claim 1, wherein the signal is an electrocardiogram signal and the signal feature is an R wave of the electrocardiogram signal.

6. The computer-implemented method of claim 1, wherein identifying changes in the body state based on the derivative further includes extracting a series of contiguous heart rate accelerations or decelerations based on the derivative.

7. The computer-implemented method of claim 6, wherein the series of contiguous heart rate accelerations or decelerations correlate to a change in a body state.

8. The computer-implemented method of claim 6, wherein identifying changes in the body state based on the derivative further includes calculating a threshold based on a count of the contiguous heart rate accelerations or decelerations in the series.

9. The computer-implemented method of claim 7, wherein identifying changes in the body state based on the derivative further includes generating a graphic representation and identifying changes in the body state as a function of the graphic representation.

10. A computer-implemented method for analyzing transitions in a body state, comprising:
    receiving a signal from an individual indicating a measurement of cardiac activity over a period of time, wherein the signal includes a signal feature that repeats in the signal;
    calculating a plurality of first intervals, wherein each first interval in the plurality of first intervals is calculated between successive signal features in the signal;
    calculating a plurality of second intervals, wherein each second interval in the plurality of second intervals is calculated between successive first intervals in the plurality of first intervals;
    calculating a derivative based on the plurality of second intervals;
    extracting a plurality of heart rate accelerations or decelerations based on the derivative; and
    identifying a transition in the body state based on the plurality of heart rate accelerations or decelerations.

11. The computer-implemented method of claim 10, further including transmitting the signal from a monitoring system associated with the individual, wherein said signal is one of an electrical signal, an acoustic signal or an optical representing the measurement of cardiac activity.

12. The computer-implemented method of claim 11, wherein receiving a signal further includes processing the signal into a plurality of waveforms, each one of said waveforms indicating a heart beat.

13. The computer-implemented method of claim 10, wherein a sign of the derivative indicates a heart rate acceleration or deceleration.

14. The computer-implemented method of claim 10, wherein identifying a transition in the body state further includes generating a graphical representation illustrating a first set of contiguous derivatives having a same sign and a second set of contiguous derivatives having a same sign, and identifying the transitions in the body state as a function of a distance between the first set of contiguous derivatives and the second set of contiguous derivatives.

15. The computer-implemented method of claim 14, wherein a set of contiguous derivatives having a negative sign correlates to a burst of sympathetic activity and having a positive sign correlates to a burst of parasympathetic activity.

16. A computer system for determining changes in a body state of an individual, comprising:
   a monitoring system configured to monitor cardiac activity;
   a signal receiving module configured to receive a signal from the monitoring system, the signal representing a measurement of cardiac activity over a period of time;
   a feature determination module configured to identify signal features that reoccur in the signal over the period of time;
   an interval determination module configured to calculate respective first intervals between successive signal features and respective second intervals between successive first intervals;
   a derivative calculation module configured to calculate a derivative of a heart rate based on the second intervals; and
   an identification module configured to identify changes in the body state based on the derivative.

17. The computer system of claim 16, wherein the monitoring system further includes a plurality of contactless sensors for monitoring cardiac activity of the individual.

18. The computer system of claim 16, wherein the signal is one of an electrical signal, an acoustic signal or an optical signal representing the measurement of cardiac activity.

19. The computer system of claim 16, the identification module further configured to extract a series of contiguous heart rate accelerations or decelerations based on the derivative.

20. The computer system of claim 19, wherein the series of contiguous heart rate accelerations or decelerations correlate to a change in a body state.

21. A non-transitory computer-readable medium storing computer-executable instructions that when executed by a computer, which includes at least a processor, cause the computer to perform a method, the method comprising:
   receiving, using at least the processor, a signal indicating a plurality of cardiac cycles of an individual over a period of time;
   detecting, using at least the processor, a signal feature, wherein the signal feature is a reoccurring event in the signal over the period of time;
   calculating, using at least the processor, a plurality of first intervals, wherein each first interval in the plurality of first intervals is calculated between successive signal features;
   calculating, using at least the processor, a plurality of second intervals, wherein each second interval in the plurality of second intervals is calculated between successive first intervals in the plurality of first intervals;
   calculating, using at least the processor, a derivative based on the plurality of second intervals; and
   identifying, using at least the processor, changes in a body state based on the derivative.

22. The non-transitory computer-readable medium of claim 21, wherein identifying changes in the body state based on the derivative further includes extracting a series of contiguous heart rate accelerations or decelerations based on the derivative.

23. The non-transitory computer-readable medium of claim 22, wherein the series of contiguous heart rate accelerations or decelerations correlate to changes in the body state.

* * * * *